United States Patent [19]

Baker

[11] 4,193,787
[45] Mar. 18, 1980

[54] BENZODIOXANE HERBICIDES

[75] Inventor: Don R. Baker, Orinda, Calif.

[73] Assignee: Stauffer Chemical Company, Westport, Conn.

[21] Appl. No.: 938,605

[22] Filed: Aug. 31, 1978

[51] Int. Cl.$^2$ .................. A01N 9/00; C07D 319/20
[52] U.S. Cl. .......................... 71/88; 71/75; 71/76; 71/77; 260/340.3
[58] Field of Search ............. 71/88, 118; 260/340.3

[56] References Cited

U.S. PATENT DOCUMENTS

| | | | |
|---|---|---|---|
| 3,792,062 | 2/1974 | Teach | 71/88 |
| 3,946,044 | 3/1976 | Richter et al. | 71/88 |
| 3,976,470 | 8/1976 | Baker | 71/118 |
| 4,007,280 | 2/1977 | Karrer | 260/340.3 |
| 4,100,296 | 7/1978 | Farooq et al. | 71/88 |
| 4,116,670 | 9/1978 | Stach et al. | 71/88 |

Primary Examiner—Glennon H. Hollrah
Attorney, Agent, or Firm—Michael J. Bradley

[57] ABSTRACT

Novel compounds are disclosed having the formula

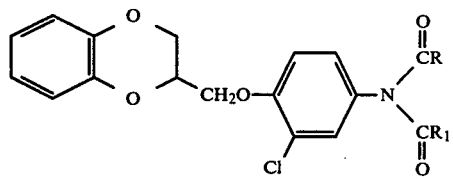

in which R and $R_1$ are independently selected from the group consisting of alkoxy having from 1 to 6 carbon atoms, preferably from 1 to 3 carbon atoms and more preferably methoxy, cycloalkyl having from 3 to 6 carbon atoms, preferably cyclopropyl and alkyl having from 1 to 6 carbon atoms, preferably having 1 to 3 carbon atoms and more preferably ethyl, which are useful as herbicides.

18 Claims, No Drawings type intermediate compound 2-benzpyranylmethyl-2-chloro-4-acylaminophenyl ether in an inert solvent such as acetone, ether, methylene chloride, chloroform, toluene or benzene. The reaction is preferably conducted at a temperature of from about −40° C. to about 30° C. Acid binding agents such as NaH may be employed.

Although the above reactions will proceed at any temperature, side reactions become more prominent at higher temperatures raising the level of impurities in the final product. For this reason, it is preferred to run the reaction at from about −40° C. to about 0° C., and most preferably at about 0° C.

The examples shown herein are illustrative of the method of preparation of both intermediates and compounds of the invention.

Specific compound preparation and herbicidal activity of the compounds of this invention are shown in the following examples.

EXAMPLE I

2-Benzpyranylmethyl-2-Chloro-4-Nitrophenyl Ethers (Intermediate)

To a mixture of 25 grams (g.) (0.15 mole) 2-hydroxymethyl-1,4-benzodioxane in 200 milliliters (ml.) dimethyl sulfoxide was added 4.6 g. (0.196 mole) sodium hydride. Then 29 g. (0.15 mole) 3,4-dichloronitrobenzone was added. The reaction was exothermic to 60° C. After the exotherm ceased, the mixture was heated to 70° C. for five minutes and then cooled to 0° C. Fifty g. of ice and 400 ml. methylene chloride were then added. The reaction mixture was then washed with ice water (200 ml.), 10 ml. 10% NaOH, 200 ml. 1 N hydrochloric acid and 100 ml. saturated sodium carbonate solution. The washed solution was dried over magnesium sulfate and evaporated in vacuo to give 44.1 g. of product having a melting point (m.p.) of 113°–114° C. The product was identified as the title product by infrared (IR) and nuclear magnetic resonance (NMR) spectra analyses.

EXAMPLE II

2-Benzpyranylmethyl-2-Chloro-4-Aminophenyl Ether (Intermediate)

Under an argon atmosphere, 22.3 g. electrolyte iron, 64 ml. ethanol and 53.4 ml. water were mixed together. To the resultant stirred mixture was added in one portion 1.88 ml. concentrated hydrochloric acid and the resulting mixture heated to reflux. Forty-four and one-tenth g. of the nitro ether prepared in Example I was added to this hot stirred mixture. The addition was made in portions of near reflux temperatures. The mixture was then refluxed for 30 minutes and 1.26 ml. of 50% sodium hydroxide solution was added. This mixture was filtered while hot through dicalite. The filtrate was concentrated in vacuo and then taken up in 200 ml. of methylene chloride, washed with two 500 ml. portions of water and four 100 ml. portions of saturated sodium carbonate solution. The washed mixture was dried over magnesium sulfate and evaporated in vacuo to yield 34 g. of product having a m.p. of 90°–91° C. The product was identified as the title product by IR and NMR analyses.

EXAMPLE III 4-(Benzo-1,4-Dioxane-2-Methoxy)-3-Chloropropionanilide (Intermediate)

The equipment and procedure were the same as Example VII with the exceptions that 3.0 g. (0.010 mole) of the intermediate of Example II, 1.67 ml. (0.012 mole) of triethylamine and 50 ml. of dichloromethane were added to the round bottom flask which was then cooled to −40° C. 0.96 ml. (0.011 mole) of propionyl chloride were then added. The reaction mixture was worked up as in Example VII and the filtrate was readily evaporated to remove solvent and obtain 3.4 g. of crystalline product having a melting point of 111°–113° C. in a yield of 97.8%. The structure was confirmed by analyses of IR and NMR as the title compound.

EXAMPLE IV

N-[4-(2-Benzodioxanemethoxy)-3-Chlorophenyl]-bis-Propion-Imide

Four and one-tenth g. (0.12 mole) of the intermediate compound prepared as in Example III, 100 ml. of dry dimethyl formamide and 0.42 g. (0.0177 mole) of sodium hydride were mixed together in a 300 ml. stirred round bottom flask at room temperature. The mixture was cooled to −20° C. and then 1.53 ml. (0.0177 mole) of propionyl chloride were added with stirring. The reaction mixture was allowed to warm to 30° C. and stand for one hour at room temperature. The liquid portion of the reaction mixture was then decanted away from the resulting solids diluted with 100 ml. of chloroform and washed with 300 ml. ice water, 300 ml. tap water and finally with 200 ml. of saturated sodium bicarbonate solution. The organic phase was dried over magnesium sulfate and evaporated in vacuo to yield 3.7 g. of a product having a $n_D^{30}$ of 1.5340.

EXAMPLE V 4-(Benzo-1,4-Dioxane-2-Methoxy)-3-Chloro-Cyclopropane Carboxanilide (Intermediate)

The equipment and procedure as in Example VII were followed with the exceptions that the round bottom flask was originally cooled to −40° C. and that 1.70 ml. (0.019 mole) of cyclopropane carboxylic acid chloride was added to the cooled round bottom flask instead of methylchloroformate. The crystals were formed in the mixture which were filtered off in vacuum and the filter was washed sequentially with water and sodium bicarbonate solution. The organic layer was dried over MgSO$_4$ and rotary evaporated to obtain crystals which were added to those previously obtained. Five and three-tenths g. of a product having a m.p. of from 144° to 148° C. were produced for a yield of 86.5%. The structure was confirmed by analyses of IR and NMR of the title compound.

EXAMPLE VI

N-[4-(2-Benzodioxanemethoxy)-3-Chlorophenyl]-bis-Cyclopropanecarboximide

The procedure was the same as used in Example II above with the exception that 4.1 g. of the intermediate compound as prepared in Example V, 0.41 g. (0.0171 mole) of sodium hydride and 100 ml. of dimethyl formamide were mixed together followed by the addition of 1.55 ml. (0.0171 mole) of cyclopropanecarboxylic acid

BENZODIOXANE HERBICIDES

BACKGROUND OF THE INVENTION

The most closely related ether to applicant's novel compounds of which applicant is aware are those disclosed in U.S. Pat. No. 3,119,682 which discloses 3-[p-(p-chlorophenoxy)phenyl]-1,1-dimethylurea. It would be readily apparent that the compound of the above cited U.S. patent is only remotely related to applicant's novel compounds due to the lack of the presence of the dioxane radical.

BRIEF DESCRIPTION OF THE INVENTION

This invention relates to novel benzodioxanes having the formula

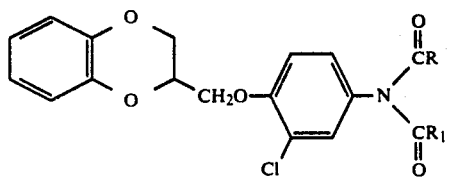

in which R and $R_1$ are independently selected from the group consisting of alkoxy having from 1 to 6 carbon atoms, preferably from 1 to 3 carbon atoms and more preferably methoxy, cycloalkyl having from 3 to 6 carbon atoms, preferably cyclopropyl and alkyl having from 1 to 6 carbon atoms, preferably having 1 to 3 carbon atoms and more preferably ethyl. The compounds are useful as herbicides when used in a herbicidally effective amount.

The term "herbicides" as used herein means a compound which control or modifies growth of plants. By the term "herbicidally effective amount" is meant an amount of compound which causes a modifying effect upon the growth of plants. By "plants" is meant germinant seeds, emerging seedlings and established vegetation, including roots and above-ground portions. Such modifying effects include all deviations from natural development; for example, killing, retardation, defoliation, desiccation, regulations, stunting, tillering, stimulation, leaf burn, dwarfing and the like.

The compounds of the present invention, as will be seen from the data which follows, have utility as post-emergence herbicides, against a wide range of plant species.

DETAILED DESCRIPTION OF THE INVENTION

Novel intermediate compounds having the formulas

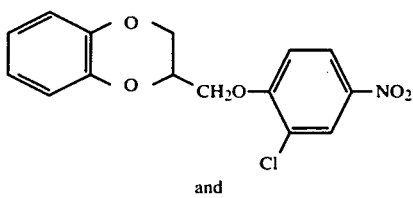

and

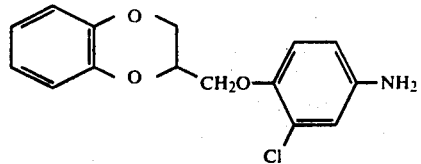

which are useful in preparing the novel herbicidal compounds of the present invention are prepared in the following general manner:

(1) 2-Benzpyranylmethyl-2-Chloro-4,4-Nitrophenyl Ether

The condensation of 3,4-dichloronitrobenzone is conducted in a polar solvent (non-reacting solvent) such as dimethylsulfoxide or water with the sodium or potassium salt of the hydroxymethyl 1,4-benzodioxane. The salt can be prepared from the alcohol and NaH or potassium t-butoxide or under certain conditions with NaOH or KOH.

(2) 2-Benzpyranylmethyl-2-Chloro-4-Aminophenyl Ether

The reduction of the nitro group of the above compound can be effected by several means such as catalytically with $H_2$ and a nobel metal catalyst or with iron in ethanol-water (50:50 by weight) using hydrochloric acid.

The novel compounds of the present invention which are defined by the formula

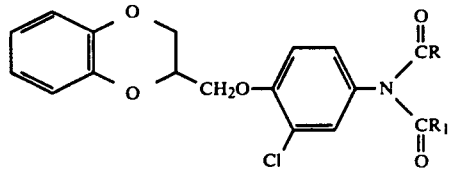

in which R and $R_1$ are independently selected from the group consisting of alkoxy having from 1 to 6 carbon atoms, preferably from 1 to 3 carbon atoms and more preferably methoxy, cycloalkyl having from 3 to 6 carbon atoms, preferably cyclopropyl and alkyl having from 1 to 6 carbon atoms, preferably having 1 to 3 carbon atoms and more preferably ethyl, exhibits herbicidal activity and are prepared from the intermediate having the formula

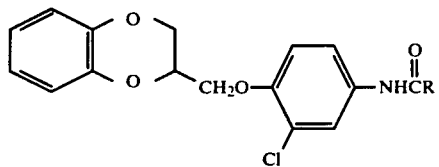

in which R and $R_1$ are independently selected from the group consisting of alkoxy having from 1 to 6 carbon atoms, preferably from 1 to 3 carbon atoms and more preferably methoxy, cycloalkyl having from 3 to 6 carbon atoms, preferably cyclopropyl and alkyl having from 1 to 6 carbon atoms, preferably having 1 to 3 carbon atoms and more preferably ethyl by reacting an appropriately substituted acid chloride with the anilide chloride. After work up, this yield 4.2 g. of a product having a $n_D^{30}$ of 1.5400.

EXAMPLE VII

O-Methyl-4-(Benz-1,4-Dioxane-2-Methoxy)-3-Chlorocarbanilate

Five g. (0.017 mole) of the intermediate product of Example II, 1.65 ml. (0.020 mole) pyridine and 50 ml. acetone were added to a 300 ml. stirred round bottom flask and cooled to a −30° C. in a dry ice acetone bath. 1.45 ml. (0.019 mole) of methyl chloroformate was added with stirring and solution was allowed to reach ambient temperature. About 50 ml. of chloroform was added to the mixture which was then washed sequentially with approximately 100 ml. of water and 100 ml. of sodium bicarbonate. The organic layer was dried over MgSO4, filtered and rotary evaporated to obtain an oil. The oil was triturated with pentane to crystallize product, yielding 5.3 g. of product having a m.p. of from 100° to 104° C. The structure was confirmed by IR and NMR analyses as the title compound.

EXAMPLE VIII

N-[4-(2-Benzodioxanemethoxy)-3-Chlorophenyl]-bis-Carbomethoxy-Imide

Four and three-tenths g. (0.0123 mole) of the intermediate compound as prepared in Example VII, 100 ml. of dry dimethyl formamide and 0.42 g. (0.0147 mole) of sodium hydride were mixed together in a 300 ml. stirred round bottom flask at −10° C. The mixture was allowed to warm to room temperature and stand for two hours. 1.14 ml. (0.0148 mole) of methyl chloroformate was added to the reaction mixture and the mixture was allowed to stand at room temperature for three hours. The reaction mixture was then filtered and the filtrate diluted with 100 ml. of methylene chloride, washed with 200 ml. ice water, 50 ml. 1 N hydrochloric acid and 100 ml. saturated sodium bicarbonate solution. The washed filtrate was then dried over magnesium sulfate and evaporated in vacuo to yield 3.5 g. of a product having a m.p. of 145°–147° C.

Compounds where R and R1 are identical can also be prepared from the aniline product of Example II by refluxing the product of Example II with 2 moles of a properly selected acid chloride in an inert solvent as defined above under the conditions stated above.

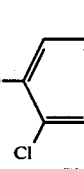

| Compound Number | R | R1 | Physical Properties |
|---|---|---|---|
| 1 | —C2H5 | —C2H5 | $n_D^{30}$ 1.5340 |
| 2 | ◁ | ◁ | $n_D^{30}$ 1.5400 |
| 3 | —OCH3 | —OCH3 | m.p. 145°–147° C. |

Herbicidal Screening Test

As previously mentioned, the novel benzodioxanes herein described are phytotoxic compounds which are useful and valuable in controlling various plant species. Compounds of this invention are tested as herbicides in the following manner.

Post-Emergence Herbicide Screening Test

On the day preceding treatment, seeds of six plant species, including hairy crabgrass [*Digitaria sanguinalis* (L.) Scop] (CG), watergrass [*Echinochloa crusgalli* (L.) Beauv.] (WG), red oat [*Avena sativa* (L.)] (RO), mustard [*Brassica juncea* (L.) Coss.] (MD), curly dock [*Rumex crispus* (L.)] (CD) and Pinto beans [*Phaseolus vulgaris* (L.)] (Bean) are planted in individual rows using one species per row across the width of the flat. The flats are placed in the greenhouse at 70° to 85° F. and watered daily with a sprinkler. About 10 to 14 days after planting when the primary leaves of the bean plants are almost fully expanded and the first trifoliate leaves are just starting to form, the plants are sprayed. The spray is prepared by weighing out 20 ml. of the test compound, dissolving it in 5 ml. of acetone containing 1% Tween 20 ® (an emulsifying agent defined as a polyoxyethylene sorbitan monolaurate) and then adding 5 ml. of water. The solution is sprayed on the foliage using a No. 152 DeVilbiss atomizer at an air pressure of 5 lb/sq. inch. The spray concentration is 0.2 and the rate is 8 lb/acre. The spray volume is 476 gallons/acre. Injury ratings are recorded 14 days after treatment. The injury rating from 0 to 100% is recorded for each species as percent control with 0% representing no injury and 100% representing complete injury.

The results of these tests are shown in Table II.

TABLE II

| Compound Number | CG | WG | RO | MD | CD | BEAN | Average % Control |
|---|---|---|---|---|---|---|---|
| 1 | 100 | 20 | 20 | 100 | 100 | 100 | 73 |
| 2 | 100 | 0 | 0 | 100 | 100 | 100 | 67 |
| 3 | 100 | 40 | 30 | 100 | 100 | 50 | 70 |

The compounds of the present invention are useful as herbicides in controlling the growth of undesirable vegetation by post-emergence application to the locus where control is desired. The compounds are generally embodied in formulations suitable for convenient application. In general, such formulations will contain inert or occasionally active ingredients or diluent carriers in addition to the active compound. Examples of such ingredients or carriers are water, organic solvents, dust carriers, granular carriers, surface active agents, oil and water, water in oil emulsions, wetting agents, dispersing agents and emulsifying agents. The herbicidal formulations generally take the form of dusts, wettable powders, granules, solutions or emulsifiable concentrates.

Dusts are free-flowing powder compositions containing the herbicidal compound impregnated on a particulate carrier. The particle size of the carriers is usually in the range of from about 30 to 50 microns. Examples of suitable carriers are talc, bentonite, diatomaceous earth and pyrophyllite. Anticaking and antistatic agents can be added, if desired. The composition generally contains up to 50% of active ingredient.

Wettable powders are finely divided compositions comprising a particulate carrier impregnated with the herbicidal compound and additionally contain one or more surface active agents. The surface active agent promotes rapid dispersion of the powder in aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols, in which the alcohol groups are free, omega-substituted polyethylene glycols of relatively long chain length. A list of surface active agents suitable for use in agriculture formulations can be found in *Pesticide Formulations* by Wade Van Valkenburg, Marcel Dekker, Inc., N.Y. 1973 at pages 79–84.

Granules comprise the herbicidal compound impregnated on a particulate insert carrier having a particle size of about 1 to 2 millimeters (mm.) in diameter. The granules can be made by spraying a solution of the active ingredient in a volatile solvent onto the granular carrier. Suitable carriers in preparation of granules include clay, vermiculite, sawdust, granular carbon, and the like.

The herbicidal compounds can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate.

The formulations described above, employing phytotoxic or herbicidally effective amounts of the compounds described herein, are applied to the loci where control is desired in any conventional manner. The loci referred to above include soil, seeds, seedlings and the actual plants. Dusts and liquid compositions can be applied by the use of power dusters, boom and hand sprayers and spray dusters. The compositions can also be applied from airplanes as dusts or sprays because they are effective in very low dosages.

The phytotoxic compositions of this invention can also contain other additaments, for example, fertilizers, pesticides, and the like, used as adjuvants or in combination with any of the above-described adjuvants. Other phytotoxic compounds useful in combination with the above-described compounds include, for example, 2,4-dichlorophenoxyacetic acids, 2,4,5-trichlorophenoxyacetic acid, 2-methyl-4-chlorophenoxyacetic acid, and the salts, esters, and amides thereof; triazine derivatives, such as 2,4-bis (3-methoxypropylamino)-6-methyl-thio-s-triazine, 2-chloro-4-ethylamino-6-isopropylamino-3-triazine, and 2-ethylamino-4-isopropylamino-6-methyl-mercapto-s-triazine; urea derivatives such as 3-(3,4-dichlorophenyl)-1,1-dimethyl urea; and acetamides such as N,N-diallyl-α-chloroacetamide, N-α-chloroacetyl) hexamethyleneamine, and N,N-diethyl-α-bromoacetamide, and the like; benzoic acids such as 3-amino-2,5-dichlorobenzoic; S-ethyldipropylthiocarbamate; S-ethyl hexahydro-1H-azepine-1-carbothioate and the like. Fertilizers useful in combination with the active ingredients include, for example, ammonium nitrate, urea and superphosphate. Other useful additaments include materials in which plant organisms take root and grow, such as compost, manure, humus, sand and the like.

The amount of a compound of the present invention which constitutes a phytotoxic or herbicidally effective amount depends upon the nature of the seeds or plants to be controlled. The rate of application of active ingredient varies from about 0.01 to about 50 pounds per acre, with the actual amount used depending on the overall cost and the desired results. It will be readily apparent to one skilled in the art that compounds exhibiting lower herbicidal activity will require a higher dosage rate for the same degree of control than more active compounds.

What is claimed is:

1. A compound having the formula

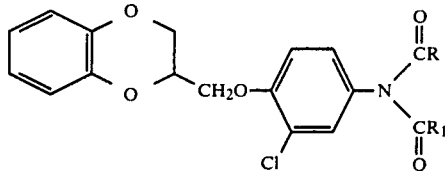

wherein R and R₁ are independently selected from the group consisting of alkoxy having from 1 to 6 carbon atoms, cycloalkyl having from 3 to 6 carbon atoms and alkyl having from 1 to 6 carbon atoms.

2. The compound of claim 1 wherein R and R₁ are independently selected from the group consisting of alkoxy having from 1 to 3 carbon atoms, cycloalkyl having from 3 to 6 carbon atoms and alkyl having from 1 to 3 carbon atoms.

3. The compound of claim 1 wherein R and R₁ are independently selected from the group consisting of —OCH₃,

and —C₂H₅.

4. The compound of claim 3 wherein R is —OCH₃ and R₁ is —OCH₃.

5. The compound of claim 3 wherein R is

and R₁ is

6. The compound of claim 3 wherein R is —C₂H₅ and R₁ is —C₂H₅.

7. A composition of matter comprising a herbicidally effective amount of the compound having the formula

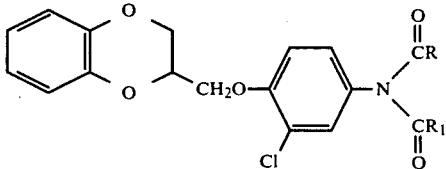

wherein R and R₁ are independently selected from the group consisting of alkoxy having from 1 to 6 carbon atoms, cycloalkyl having from 3 to 6 carbon atoms and alkyl having from 1 to 6 carbon atoms; and an inert carrier.

8. The composition of claim 7 wherein R and $R_1$ are independently selected from the group consisting of alkoxy having from 1 to 3 carbon atoms, cycloalkyl having from 3 to 6 carbon atoms and alkyl having from 1 to 3 carbon atoms.

9. The composition of claim 7 wherein R and $R_1$ are independently selected from the group consisting of —$OCH_3$,

and —$C_2H_5$.

10. The composition of claim 9 wherein R is —$OCH_3$ and $R_1$ is —$OCH_3$.

11. The composition of claim 9 wherein R is

and $R_1$ is

12. The composition of claim 9 wherein R is —$C_2H_5$ and $R_1$ is —$C_2H_5$.

13. A method of controlling undesirable vegetation comprising applying to the locus thereof a post-emergent herbicidally effective amount of the formula

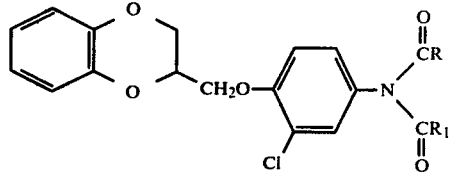

wherein R and $R_1$ are independently selected from the group consisting of alkoxy having from 1 to 6 carbon atoms, cycloalkyl having from 3 to 6 carbon atoms and alkyl having from 1 to 6 carbon atoms.

14. The method of claim 13 wherein R and $R_1$ are independently selected from the group consisting of alkoxy having from 1 to 3 carbon atoms, cycloalkyl having from 3 to 6 carbon atoms and alkyl having from 1 to 3 carbon atoms.

15. The method of claim 13 wherein R and $R_1$ are independently selected from the group consisting of —$OCH_3$,

and —$C_2H_5$.

16. The method of claim 15 wherein R is —$OCH_3$ and $R_1$ is —$OCH_3$.

17. The method of claim 15 wherein R is

and $R_1$ is

18. The method of claim 15 wherein R is —$C_2H_5$ and $R_1$ is —$C_2H_5$.

* * * * *